United States Patent
Hull, Jr.

(10) Patent No.: US 12,115,211 B2
(45) Date of Patent: Oct. 15, 2024

(54) VITAMINS AND ALPHA KETO ACID COMPOSITIONS FOR USE IN A TREATMENT PROGRAM FOR CHRONIC KIDNEY DISEASE PATIENTS

(71) Applicant: Edgar Lee Hull, Jr., Verona, WI (US)

(72) Inventor: Edgar Lee Hull, Jr., Verona, WI (US)

(73) Assignee: Edgar Hull, Verona, WI (US)

( * ) Notice: Subject to any disclaimer, the term of this patent is extended or adjusted under 35 U.S.C. 154(b) by 0 days.

(21) Appl. No.: 17/945,054

(22) Filed: Sep. 14, 2022

(65) Prior Publication Data

US 2023/0028626 A1    Jan. 26, 2023

Related U.S. Application Data

(62) Division of application No. 17/061,952, filed on Oct. 2, 2020, now Pat. No. 11,484,579.

(51) Int. Cl.

| | | |
|---|---|---|
| *A61K 38/44* | (2006.01) |
| *A61K 31/122* | (2006.01) |
| *A61K 31/197* | (2006.01) |
| *A61K 31/198* | (2006.01) |
| *A61K 31/355* | (2006.01) |
| *A61K 31/405* | (2006.01) |
| *A61K 31/4172* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/714* | (2006.01) |
| *A61K 33/00* | (2006.01) |
| *A61K 33/04* | (2006.01) |
| *A61K 33/30* | (2006.01) |

(52) U.S. Cl.
CPC .......... *A61K 38/443* (2013.01); *A61K 31/122* (2013.01); *A61K 31/197* (2013.01); *A61K 31/198* (2013.01); *A61K 31/355* (2013.01); *A61K 31/405* (2013.01); *A61K 31/4172* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/714* (2013.01); *A61K 33/00* (2013.01); *A61K 33/04* (2013.01); *A61K 33/30* (2013.01); *A61K 38/446* (2013.01)

(58) Field of Classification Search
None
See application file for complete search history.

(56) References Cited

U.S. PATENT DOCUMENTS

| 11,253,496 B2 | 2/2022 | Hull, Jr. |
| 11,484,579 B2 | 11/2022 | Hull, Jr. |
| 2005/0100613 A1 | 5/2005 | Giordano |
| 2009/0074883 A1* | 3/2009 | Gupta ................... A23L 33/175 424/643 |
| 2016/0367621 A1* | 12/2016 | Demopoulos ........ A61K 9/0053 |

FOREIGN PATENT DOCUMENTS

| CN | 104187720 A | 12/2014 |
| EP | 0 747 395 A1 | 12/1996 |
| EP | 3799724 B1 | 8/2022 |
| WO | WO2002026221 A2 | 4/2002 |
| WO | WO 2014/199333 | * 12/2014 |
| WO | WO 2018208846 | * 11/2018 |
| WO | WO2019108809 A2 | 6/2019 |

OTHER PUBLICATIONS

Majumder et al. "Hydroxy Propyl Methyl Cellulose: Different Aspects in Drug Delivery" 2016.*
U.S. Appl. No. 17/061,952 first office action on the merits mailed on Apr. 14, 2022.
Notice of Allowance of U.S. Appl. No. 17/061,952 mailed on Aug. 12, 2022.
F. M. Iorember, "Malnutrition in Chronic Kidney Disease", Front Pediatr. Jun. 20, 2018; 6: 1-9.
A.A. House et al., "Effect of B-Vitamin Therapy on Progression of Diabetic Nephropathy. A Randomized Controlled Trial", JAMA. Apr. 28, 2010;303(16):1603-1609.
H.F. Tbahriti et al., "Effect of Different Stages of Chronic Kidney Disease and Renal Replacement Therapies on Oxidant-Antioxidant Balance in Uremic Patients" Biochemistry Research International, pp. 1-9.
B.A. Zachara et al., "Selenium and glutathione peroxidases in blood of patients with different stages of chronic renal failure", J Trace Elem Med Biol. 2004; 17(4):291-9. Abstract.
E.E. van de Lagemaat, "Vitamin B12 in Relation to Oxidative Stress: A Systematic Review", Nutrients 2019, 11, 482.

(Continued)

*Primary Examiner* — Danah Al-Awadi

(57) ABSTRACT

A vitamin for use by kidney patients in Stages 3, 4, 4a, 4b, and 5, who are not on dialysis, comprising administering daily a: low nitrogen diet; low nitrogen protein food comprising magnesium and/or calcium salts of alpha keto acids; and time released vitamin. The vitamin comprises the active ingredients of: Zinc; Selenium; Vitamins B1, B2, B6, B12, B5, E, and K2; Niacin; superoxide dismutase; catalase; glutathione and Folate; and excludes calcium, magnesium, phosphorus, sodium, manganese, fluoride, Vitamin D and K1. The low nitrogen food contains daily up to 300 mg of nitrogen; and at least five alpha keto analogues of magnesium and/or calcium salts of: leucine, isoleucine, methionine (MEMS-II), phenylalanine (PAMS-I), and valine. Methods of making and the chemical structures MEMS-II and the PAMS-I are disclosed. The treatment results in an increase of Glomerular Filtration Rate (GFR), a decrease in blood urea levels, and a decrease in creatinine levels.

5 Claims, 7 Drawing Sheets

(56) References Cited

OTHER PUBLICATIONS

S.R. Lee, "Critical Role of Zinc as Either an Antioxidant or a Prooxidant in Cellular Systems", Hindawi Oxidative Medicine and Cellular Longevity, 2018, pp. 1-12.

G.E. Arteel, H. Sies, "The biochemistry of selenium and the glutathione system", Environ Toxicol Pharmacol. Sep. 2001;10(4): 153-8.

EPO search report 139939 for appl. EP20199876, issued Feb. 15, 2021, entitled "Vitamins and Alpha Keto Acid Compositions for Use in a Treatment Program for Chronic Kidney Disease Patients".

* cited by examiner

Route of synthesis of MEM-II

Stage I

Stage II

Route of synthesis PAM-I

TABLE 8

| Patient # | GFR T=0 | GFR- 90 days | BUN T=0 | BUN- 90 days | Creatine T=0 | Creatine- 90 days |
|---|---|---|---|---|---|---|
| Patient 1 | 41 | 57 | . | . | . | . |
| Patient 2 | 28 | 35 | . | . | . | . |
| Patient 3 | 13 | 16 | 29 | 18 | 1.29 | 0.97 |
| Patient 4 | 59 | 66 | . | . | . | . |
| Patient 5 | 44 | 56 | 31 | 20 | 1.39 | 1.19 |
| Patient 6 | 30 | 39 | 34 | 19 | 1.8 | 1.33 |
| Patient 7 | 33 | 43 | 35 | 17 | 1.35 | 1.06 |
| Patient 8 | 38 | 56 | 27 | 15 | 1.48 | 1.18 |
| Patient 9 | 45 | 52 | . | . | . | . |
| Patient 10 | 47 | 57 | . | . | . | . |
| Patient 11 | 45 | 63 | . | . | 1.8 | 1.6 |
| Patient 12 | 48 | 59 | 33 | 16 | 1.34 | 1.14 |
| Patient 13 | 34 | 44 | 39 | 27 | 1.85 | 1.51 |
| Mean | 38.85 | 49.46 | 32.57 | 18.86 | 1.54 | 1.25 |
| % Change | 27.33 | | -42.11 | | -18.86 | |

FIG. 4

VITAMINS AND ALPHA KETO ACID COMPOSITIONS FOR USE IN A TREATMENT PROGRAM FOR CHRONIC KIDNEY DISEASE PATIENTS

CROSS-REFERENCE TO RELATED APPLICATION

This application is a divisional of U.S. patent application Ser. No. 17/061,952, filed on Oct. 2, 2020, the entire disclosure of which is hereby enclosed by reference in its entirety.

FIELD OF THE INVENTION

The present invention relates to compositions, methods of making, and a treatment plan to slow kidney disease progression composed of a low nitrogen diet, low nitrogen protein food and low dose vitamin with direct antioxidant supplementation to comprise a complete method for safely slowing kidney disease progression while ensuring all recommended daily amounts of vitamins, minerals and essential amino acids are met. Treatment plan is for Chronic Kidney Disease Patients in Stage 3, 4a, 4b, and 5 who are not on dialysis and who are on a low protein diet as disclosed herein.

BACKGROUND OF THE INVENTION

Kidney disease diets have never been proven to slow kidney disease progression to a clinical standard. Low protein and very low protein diets have been attempted with mixed results. The primary reason for failure is the lack of a standardized, quantifiable and measured approach to nutrition, systemic causes of kidney disease and not reducing the workload on kidney's enough to get measurable results so that blood and urine tests can return to the normal ranges. A variety of problems exists with past approaches, which often results in several forms of malnutrition: protein energy, uremic, traditional malnutrition, and Malnutrition-Inflammation-Atherosclerosis (MIA) syndrome. Malnutrition is a common driver of kidney disease progression and the largest factor in the quality of life for kidney patients. No known products have been developed that are safe and effective for stage, 3, 4a, 4b, and 5 patients who are not on dialysis. These patients need a detailed, coordinated approach to ensure nutrition needs are met while they attempt to slow or stop the progression of incurable kidney disease. The present invention comprises three parts: a low nitrogen diet, low nitrogen protein food and low dose controlled release vitamin with direct antioxidant supplementation as a part of a treatment/strategy to slow the progression of incurable chronic kidney disease by minimizing waste product workload and metabolic management duties normally performed by healthy kidneys. Diseased kidneys are already taxed and unable to keep related blood and urine tests in the normal range. An approach is needed that takes all of these factors into consideration to maximize nutrition and minimize kidney workload.

Problem in the Prior Art—Vitamins and Diet

Depending on the study, anywhere from 20% to 80% of kidney patients not on dialysis suffer from some form of malnutrition. A conservative number is 50% of all kidney patients suffer from some form of malnutrition. Malnutrition is a strong mortality indicator and increases the risk of death, speed of kidney disease progression, number of comorbid conditions and reduces quality of life. Obtaining proper nutrition while minimizing kidney workload is a major challenge for kidney disease patients [1]. The low protein and very low protein diets that kidney disease patients pursue in the name of reducing kidney workload are often counterproductive because they result in malnutrition, which speeds the progression of kidney disease or comorbid conditions like soft tissue calcification. Protein malnutrition and B vitamin malnutrition are also common on these diets. Many doctors, patients, nutritionists and others do not recommend low protein or very low protein diets due to malnutrition concerns.

Dialysis vitamins: in the past, vitamins or micronutrient supplements for kidney patients have been targeted to dialysis patients only. No product has existed for patients who are not on dialysis, or for patients on a prescribed diet to slow the progression of kidney disease. Dialysis vitamins contain very high doses of many ingredients, such as 500% of the Recommended Dietary Allowance (RDA) (e.g., 500% to 600% of vitamin B6, 200% of folic acid, 250% of vitamin D, etc.). This is of major importance for the following reasons: 1) large doses of the B vitamins have been shown to increase the speed of kidney disease progression in those who are not on dialysis; 2) large doses of folic acid may increase the risk of heart attack; 3) heart disease is the number one killer of kidney patients; 4) vitamin D supplementation is not recommended unless patients are very low in vitamin D, and supplementation of vitamin D may increase the speed of kidney disease progression; and 5) high doses of vitamin C may contribute to kidney stones. This list goes on, but kidney patients NOT on dialysis should not be taking dialysis vitamins.

Dialysis vitamins contain very high doses of many vitamins due to the fact that the dialysis process reduces many of the water-soluble vitamins. These large doses are needed for dialysis patients who are undergoing dialysis several days a week. The excess of vitamin overload is removed every other day during dialysis. However, the same vitamin that is beneficial to dialysis patients is very risky for kidney patients not on dialysis. The excess vitamins and minerals build up the patient's systems if they cannot be managed successfully by the kidneys. Management of these levels and excretion is often handled by the kidneys. Diseased kidneys cannot be expected to dispose of two to ten times the RDA of certain vitamins.

In addition, almost all scientific literature is in agreement that high doses of vitamins above the RDA only carries risks with little to no documented benefits. A review of related studies with an emphasis on clinical trials can be summarized as follows: both fat and water-soluble vitamins above the RDA may cause adverse effects, which include increasing risk of mortality and not providing any measurable benefit to the patient [2].

To achieve proper nutrition while lowering kidney workload, there is a need for an evidence-based system for nutrient consumption that can safely promote kidney health. Indeed, our research has shown that the primary contributing factor for the failure of kidney disease diets is a lack of a coordinated approach to nutrition. Other important factors include: 1) malnutrition begins early in stage 2 and 3; 2) the risk of hospitalization and mortality are inversely correlated to nutritional markers; and 3) patients need exact guidance and recommendations as they are managing contradictory goals balancing between too little or too much of many substances.

No proven and measurable treatment exists to reduce the speed of kidney progression. The current practice is kidney disease patients are monitored until the need for dialysis or transplant is imminent. This period of time between diagnosis and dialysis can be two to twenty years. During this time period, no proven and measurable treatment exists to increase the useful life of kidneys.

Traditional kidney diets focus on normal amounts of protein and nitrogen intake while managing potassium, phosphorus and sodium. The high nitrogen content of these diets does not allow blood urea nitrogen, creatinine or GFR levels to change meaningfully and does not slow kidney disease. Dietary nitrogen for 60 grams of dietary protein exceeds 9,000 mg per day, far in excess of what diseased kidneys can process. Many kidney diets increase protein intake to 1 to 1.2 grams per kg exceeding 12,000 mg per day. In addition, these diets do not address over twenty plus drivers of kidney disease progression, which continues unabated until a kidney transplant or dialysis is required.

Low protein diets (LPD) and very low protein diets (VLPD) have been experimented with for the past 30+ years with unpredictable results. There is no published standard for LPD and VLPD diets. These diets are also random in nature, thus increasing failure rates. Patients are given very little if any instruction and expected to comply. LPD and VLPD diets have been considered failures due to lack of any measurable impact on blood test results. The costs of these diets are also considered very high due to the specialized food used. There is a great need for a standardized approach that can be proven in clinical trials.

The risk of malnutrition is a risk for any special diet, but this risk is much more severe in kidney patients. Depending on vitamin, mineral, protein, etc., kidney disease patients may not be able to safely manage excess amounts of the consumed vitamins, minerals and proteins. In the best case overnutrition does no harm; but overnutrition of essential amino acids may carry significant health risks. And in the worst case overnutrition speeds the progression of both kidney and heart disease progression.

Traditional kidney diets, including LPD and VLPD diets, may cause more harm than good. One aspect of a diet or protein may cancel any possible benefits from these diets or protein supplements. For example, a patient uses a calcium based keto analog/amino acid blend to supplement a low protein diet, and this is what happens in real life. A patient consumes 50 grams+ or 1.7 ounces+ (a very small amount) of chicken, beef, fish, eggs, pork, etc. and completely erases any reduction in nitrogen load provided by the keto-analogue amino acid blend. In addition, past approaches recommended 100% of daily RDA for protein supplementation. This leads to much higher than needed nitrogen loads with no known benefit. Nitrogen workload increases by over 1,500 mg by this small change negating any benefit from low nitrogen keto analogues.

In another example, the average American consumes 1029 mg of calcium per day according to the USDA. The recommended daily amount is 800 to 1,200 mg of calcium from all sources both dietary and supplemental. Calcium based keto-analogues/amino acids blends require patients to consume 700 to 1,300 mg of supplemental calcium per day. Supplemental calcium intake is implicated in soft tissue and vascular calcification and increased mortality rates. This is important as vascular calcification is the number one killer of kidney patients. Hence, it is currently impossible for patients not to greatly exceed the RDA for calcium using existing keto-analogue amino acid blends.

Diets, treatment plans, protein foods, and vitamins do not address the primary drivers of kidney disease progression. Kidney disease is systemic in nature and must be treated as systemic conditions. These prior art diet plans and supplements only address one or two drivers of kidney progression, which does not work. Albuminuria, proteinuria, diabetes and kidney disease progression are greatly affected by antioxidant status. Antioxidant status is not addressed by any known treatment or diet [3]. Direct supplementation of primary antioxidants is the most effective way to address the reduction in systemic antioxidants, superoxide dismutase (SOD), glutathione (GSH) and catalase (CAT). As kidney disease progresses, primary antioxidant levels drop proportionally. Indirect supplementation fails to recognize the antioxidant dysfunction caused by kidney disease. Treating or reducing the effects of this dysfunction must be part of any effective treatment plan or diet [4].

The random nature of past approaches contributes to failure rates of all related prior art plans, diets, protein foods, vitamins and so on. This also adds to confusion among caregivers and patients. Thousands of combinations are possible when everything is allowed and no standards exist. Patients cannot be expected to become nutritionists, chefs and physicians overnight. The work for this must be done for patients so that a proven and measurable plan can be used. Without short-term measurable results, most patients abandon these approaches. It is critical for patients to be able to show measurable progress through blood tests in a short amount of time or they will not continue with treatment in most cases. What is needed in the art is a coordinated treatment program for kidney patients who are not on dialysis, comprising: a prescribed low nitrogen diet; a low nitrogen protein food; and a multivitamin. It is beyond the scope for dietitians, nutritionists and medical professionals to calculate fifty plus nutritional requirements, correct antioxidant status and develop a healthy low nitrogen diet and treatment plan that can produce clinical results. A quantifiable approach is needed.

SUMMARY OF THE INVENTION

The present invention comprises a prescribed low nitrogen diet, low nitrogen protein food (Albutrix™) matched to the diet and the specific stage of kidney disease nutrition, and a low dose-controlled release multivitamin to address any deficiencies in dietary intake. Direct supplementation of primary antioxidants, GSH, CAT and SOD are supplemented with the vitamin to increase effectiveness and allow for lower doses, which increase safety. The result is a vitamin composition, protein food composition and a prescribed diet that complete a multi-step treatment program for use in a safe and low risk treatment program designed to slow kidney disease progression in Chronic Kidney Disease Patients in Stage 3, 4, 4a, 4b, and 5 who are NOT on dialysis and who are on a low protein or prescribed diet as disclosed herein.

These three elements work synergistically together in an unexpected manner to ensure safe, long term treatment that results in an average 42% reduction in blood urea nitrogen, 23% reduction in creatinine, 28% increase in GFR, lower Prograf doses for transplant patients not on dialysis and a reduction in the number of comorbid conditions. After a 28% increase in GFR, one year later GFR levels are still increased showing a slowing of disease progression. The combination of increasing GFR and maintaining the increased GFR long term work together to dramatically slow kidney disease progression in kidney disease and kidney transplant patients. This has not been demonstrated in the prior art by any kidney disease treatment/plan/diet or vitamin.

All of the elements (i.e. Kidney factor diet, protein food (Albutrix™) and vitamin (Microtrix™)) work synergistically together to allow dramatic, but safe improvements in kidney patients outcomes in 90 days or less. Long term treatment over 18 months shows safety and improvements continuing for 12 to 18 months. Resulting GFR increases can be as high as 70% from lows. Blood and urine tests continue to improve over long periods. However, if any one element in the treatment plan is removed, then improvements slow or stop or malnutrition issues may develop. All three elements are required to ensure kidney disease progression is slowed dramatically, the useful life of kidneys is extended by years and nutrition markers/goals are met to ensure long term safety.

The vitamin composition comprises, consists essentially of, or consists of: i) the active ingredients: Zinc; Selenium; B1-Thiamine; B2-Riboflavin; Niacin; B6 Pyridoxine; Folic Acid; B12; B5; Vitamin E; and K2, superoxide dismutase; catalase; and glutathione and ii) excluding all of the following: calcium (Ca); magnesium (Mg); phosphorus (P); sodium (Na); manganese (Mn); fluoride (F); Vitamin D; and Vitamin K1.

In an embodiment, the vitamin further comprises an antioxidant component that compensates for an increase in oxidative stress and reduced antioxidant capacity noted in kidney disease. The body's main antioxidants of catalase (CAT), glutathione (GSH) and superoxide dismutase (SOD) drop proportionally as kidney disease progresses. In order to actively reduce the speed of kidney disease progression antioxidant therapy is needed as kidney disease progression is correlated to oxidative stress status. Liposomal forms of CAT, GSH and SOD must be used in order to ensure absorption. Vitamin supplementation of selenium, zinc and B12 is necessary if GSH and SOD are supplemented. If zinc or selenium are deficient, antioxidant supplementation can be impaired or reduced [5]. Partial supplementation is not an adequate solution. All past solutions only address one aspect of kidney disease, not all known issues contributing to kidney disease progression.

In the various embodiments, the low nitrogen protein food comprises, consists essentially of, or consists of one of the Albutrix™ compositions S3, S4a, S4b, and S5 in a tablet formulation, as disclosed in Tables 4-7.

The present invention further comprises a chemical structure and method of making the alpha keto analogue of magnesium methionine (MEMS-II); and the alpha keto analogue of magnesium phenylalanine (PAM-I).

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 4 is table displaying the data taken for twelve patients before taking one of the formulations Albutrix™ in Tables 1-4 herein, and 90 days thereafter to measure changes in their GFR, blood urea and creatinine levels.

Figure 1:
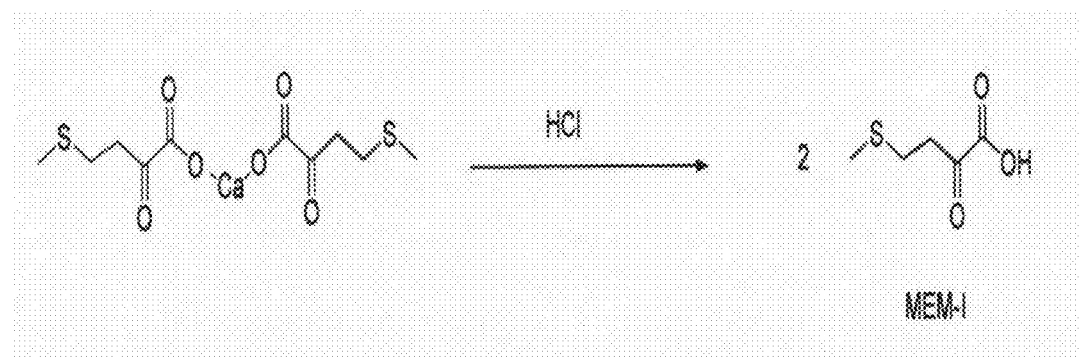
FIG. 1 is an illustration of the chemical structures in the route of synthesis for the production of the keto acid of methionine as magnesium salt (MEM II) compound in a two-step process.
Figure 1:
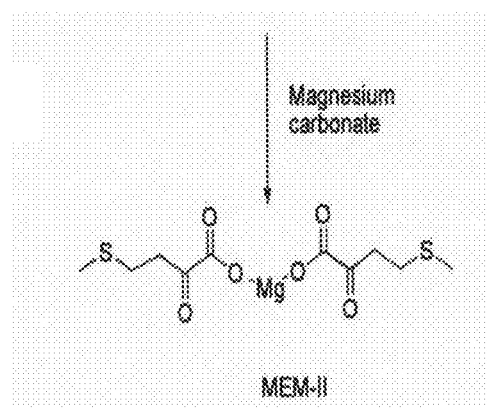

Appendix A provides the steps in a method of making the keto acid of methionine as magnesium salt (MEMS II), and in a method of making a keto acid of phenylalanine salt as a magnesium salt (PAM).

DETAILED DESCRIPTION OF EXEMPLARY EMBODIMENTS

Glossary of Terms

The term "alpha keto acid" refers to an alpha ketocarboxylic acid form, or "keto-analog" of an essential amino acid (EAA) (e.g., histidine, isoleucine, leucine, lysine, methionine, phenylalanine, threonine, tryptophan, and valine) or non-essential amino acid (non-EAA) (e.g., tyrosine) formed by the amine group being substituted by a ketone. Keto acids or keto amino acid blends have distinct advantages over traditional dietary protein consumption and traditional amino acid supplements. These benefits only apply to those patients with impaired amino acid or protein metabolism. In most cases, this impairment is related to handling protein metabolic products kidney, liver, aging, inflammation or microinflammation, metabolic acidosis, oxidative stress or related diseases.

As used herein, the term "about" refers to +/−10 percent of the stated number or value. The term "substantially" means significantly the same as recognized by one of ordinary skill in the art.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus, in some embodiments not otherwise explicitly recited, any instance of "comprising" may be replaced by "consisting of" or, alternatively, by "consisting essentially of."

Treatment Programs

Disclosed herein is a multicomponent treatment program as illustrated in Table 1 to allow kidney disease patients to meet all RDA's while not exceeding them while on a low protein diet. Any solution must have the following characteristics to be beneficial to kidney patients who are NOT on dialysis.

TABLE 1

| Component | Treatment Program/Protocol |
| --- | --- |
| C1 | Prescribe a low nitrogen diet treating drivers of kidney disease progression with all vitamin/mineral calculated/measured. Dietary nitrogen intake should not exceed 4,800 mg of total nitrogen per day. This includes nitrogen from any protein supplementation. |
| C2 | Administer a Low nitrogen protein food (Albutrix ™) with all essential amino or keto acids measured against dietary intake with less than 300 mg of nitrogen for an average daily dose. |
| C3 | Administer a Vitamin/mineral/antioxidant supplement based on dietary intake to get to 100% of the RDA's, compensate for reduction in antioxidants and keep total calcium intake at or below RDA's. |
| C4 | Low dose and time release to spread the kidney workload over the longest period of time and reduce the odds that any one vitamin or mineral will build up in the patient's system (e.g. 3-5 hours). |
| C5 | Eliminate/remove vitamins/minerals that are known to be problematic for kidney patients or known to build up in the body. |

Component One (C1): A prescribed diet must be known and defined. No method of supplementation can be successful unless dietary intake is known. There is no way to ensure nutrition unless current dietary nutrition is quantified. All past approaches make recommendations with no knowledge of dietary intake. In our case, the prescribed diet is a low nitrogen/protein, high nutrition diet described in the "Stopping Kidney Disease Food Guide", 2017, by the present inventor, the entirety of which is hereby incorporated in by reference [9]. While patient compliance with diets is never 100%, 80% to 90% compliance is common for patients who chose this treatment approach. A prescribed diet allows all vitamins, minerals, protein, nitrogen, etc. to be measured and managed. Further details are provided infra. Total dietary nitrogen intake should not exceed 4,800 mg of nitrogen per day from all sources including protein supplementation.

Component Two (C2): A low nitrogen protein food (e.g. less than 300 mg/daily of nitrogen=6 pills per day of Albutrix S3, 4, 4a, 4b, and 5) must be used to ensure protein nutrition and stay within RDA's so that risk is not increased and to reduce the workload on the kidneys. Using a low nitrogen protein food like Albutrix™ allows the patients to stay within the recommended daily amounts. For example, traditional keto analogs, also called keto acids, lower nitrogen intake is at the expense of calcium intake. Daily supplemental calcium intake is between 750 mg and 1,200 mg using traditional keto analogs. The average daily intake of calcium is between 800 and 1,000 mg in the United States. This matches the recommendation of the National Kidney Foundation 800 mg to 1,200 mg per day from all sources both dietary and supplemental. This fact means patient intake using traditional keto analogs can be upwards of 2,000 mg per day, more than double the RDA. Supplemental calcium intake is not recommended due to accelerated soft tissue calcification including vascular calcification. Products like Albutrix™ contain no supplemental calcium or very low supplemental calcium so that patients can stay at or below the RDA for each vitamin and mineral. Albutrix™ allows patients to control calcium and magnesium intake while ensuring protein nutrition. Any protein supplement must allow patients to control intake and not exceed the RDA so risks are not increased. In addition, a supplemental nitrogen intake should be less than 300 mg per day to effectively reduce blood urea nitrogen levels. When supplementation nitrogen intake exceeds 500 mg per day, it becomes increasingly hard for patients to comply with dietary recommendations. If supplemental nitrogen exceeds 750 mg per day, it becomes impossible for the average patient.

Component Three (C3): The vitamin compositions V1-3 of the present invention must solve for any deficiencies due to Component C1 and C2. The recommended dietary amount (RDA) minus dietary intake equals the appropriate vitamin, mineral or essential amino acid/keto analog. For example, if 100% of vitamin C intake is being met by the prescribed diet, no vitamin C is needed in the vitamin. Another example, if dietary vitamin B12 is at 30% of recommended daily allowance from diet, then only 70% of the recommended daily amount should be contained in the vitamin. Low B vitamins are common in vegan or vegetarian low protein diets. Amino acids that are made by the body and not impacted by kidney disease do not need to be supplemented. Amino acids that cannot be excreted normally due to reduced kidney function should not be supplemented. Example, amino acid L-ornithine and L-citrulline should not be supplemented in non-dialysis kidney patients. All kidney patients run high in this amino acid as excretion is impaired. Other nonessential amino acids like L-Tyrosine should only be supplemented in stage 5 kidney disease patients, but rarely in stage 4 and never in stage 3.0 The combination of a well thought out, measured and coordinated approach to nutrition allows safe long term use to slow kidney disease progression. Albutrix™ allows no supplemental calcium intake or intake lower than 200 mg per day using Albutrix™ S4 or zero calcium content for Albutix S3. This allows patients to stay within the recommended RDA's. Antioxidant supplementation of CAT, GSH and SOD are administered with the vitamin to ensure adequate selenium, B12 and zinc levels are present. A synergistic effect occurs when all three are supplemented, CAT, GSH and SOD and again with GSH and selenium and SOD and zinc [6-8]. Lower doses can be used in this case which increases long term safety.

Component Four (C4): Vitamin three (V3) should be a combination of low dose and time release. Low dose ensures the kidneys are not overloaded with metabolic waste products due to large single doses. Time release is another step to ensure the workload is spread over a longer period of time. Compare taking 500% of the RDA at one time with taking 50% of the RDA spread over five to six hours. This is a dramatic difference in waste product workload and management. One is 500% of the RDA in one-hour versus 10% of the RDA per hour. Kidneys operating at 20% of normal capacity cannot successfully process large doses over a short period of time. Vitamin V3 and mineral amounts should be as a low dose and the release must be spread over a long period of time (e.g. controlled time release formulation).

Component Five (C5): Questionable or problematic vitamins/minerals should not be used in a daily vitamin. Many patients have trouble managing vitamin D, iron, calcium, phosphorus, magnesium and others. These problematic vitamins/minerals must be dealt with by a qualified physician, regular blood testing and targeted or specific nutrition or supplements. Example: Vitamin K supplementation is not recommended due to the relationship to blood thinning drugs. Too much vitamin K can impair the effectiveness of blood thinners. Example: low or high levels of vitamin D increase the speed of kidney disease progression and when treated many times one pill a week is all that is needed. Patients in the sun belt in retirement received a very different amount of sunlight compared with patients in the North or Northeast. The following is a list of vitamins or minerals that should not be included in any daily vitamin or mineral supplement for kidney patients not on dialysis: calcium (Ca); magnesium (Mg); phosphorus (P); sodium (Na); manganese (Mn); fluoride (F); Vitamin D; and Vitamin K1. And any other vitamin or mineral when daily dietary intake is greater than the recommended daily amount or that build up in kidney patients.

Meet or match recommended amounts of daily recommended amounts (RDA)set by the leading health organizations like: the National Institutes of Health, the World Health Organization, the National Kidney Foundation, the American Heart Association, the American Academy of nutrition and dietetics, and Guidance from over 20+ countries for keto analogue use.

Component C1: Prescribed Diet
Kidney Factor Diet

The first problem is a prescribed diet that treats or manages as many comorbid conditions as possible. The reason a prescribed diet must always be first is that protein and vitamin nutrition cannot be calculated until dietary intake is known and quantified.

No known or prescribed diet for kidney patients has been proven to improve GFR and reduce the speed of kidney disease progression until now. A large part of the success of the present invention is the ability to treat/manage many of the factors that increase the speed of kidney disease progression and increase the factors that slow kidney disease progression.

The following factors in Table 2 may increase the speed of kidney disease progression and are treatable at least in part by following a strict diet and treatment plan, as prescribed herein.

TABLE 2

| | |
|---|---|
| Uremia | Hypercalcemia |
| Uremic toxins | Hypermagnesemia |
| Inflammation | Blood pressure |
| Acidosis/Renal acid load | Advanced Glycation end |
| Low serum albumin | products (AGE's) |
| Proteinuria | Hyperlipidemia |
| Sodium | Endothelial dysfunction |
| Phosphorus | Methionine restriction |
| Potassium | Heart disease |
| Oxidative stress | Type 2 diabetes |
| Weight | Uremic malnutrition |
| Kwashiorkor | Marasmus |

Dietary intake affects all of the comorbid conditions listed. This is the reason a prescribed diet is needed and not a random one. The following diet referred herein to as the "kidney factor diet" is based on addressing as many conditions as possible to increase the useful life of a patient's kidneys.

The prescribed daily diet guidelines are as follows, on a daily basis, a patient should not exceed the maximum limits for:
1) Dietary protein restriction of 0.4 grams per kg of plant-based protein (egg whites are allowed);
2) Sodium limit of 2,200 mg per day;
3) Plant based phosphorus limit of 1,200 mg per day;
4) Low or no advanced glycation end product (AGE's) consumption;
5) Net negative renal acid load for the day measured by Potential Renal acid load or PRAL formula; and
6) Eliminate or reduce supplemental calcium intake if calcium is in the normal range of 8-10 mg/dL (2-2.5 mmol/L).

The prescribed daily diet guidelines are as follows, on a daily basis, further comprise:
1) Antioxidant intake of 30,000 Oxygen radical absorbance capacity (ORAC)units or higher;
2) Polyphenol intake of 1 gram per day or higher;
3) Dietary nitrate intake 150 mg or more;
4) Dietary fiber intake of 30 grams or more;
5) Low saturated fat intake;
6) Eliminate foods not considered heart healthy, such as trans fats and high glycemic processed low protein foods; and
7) Dietary nitrogen intake of 4,800 mg or less per day when all sources of protein are factored including protein supplementation.

The only way to achieve desired intake of 100% of nutritional goals met while reducing kidney workload by 60% to 90% and treating comorbid conditions that drive kidney disease progression is with a prescribed diet, which demonstrates measurable results in less than 90 days. The summary of diet criteria may not show the logic behind each criteria. Recommended protein intake starts at 0.4 grams per kg of body weight. In general, VLPD diets recommend 0.3 grams per kg of body weight. However, the daily nitrogen load is lower on the Kidney Factor Diet at 0.4 grams per kg of body weight due to food/diet selection and using a lower nitrogen protein food (Albutrix™) Kidney Factor Diet eliminates high nitrogen plant-based foods like grains, beans and others. A large difference exists between eating 0.3 grams per kg vs 0.4 grams per kg as diet options increase dramatically every time you increase the allowed protein amounts. However, at the same time you must lower nitrogen loads to the lowest levels possible without contributing to any forms of malnutrition.

Nitrogen conversion factors to calculate nitrogen content average 6.25 with a range of 5.4 to 6.5. Plant based diets nitrogen conversion factor is 4.4, however with proper selection nitrogen conversion factors are as low as 3.8 to 4. This represents a 35% to 50% reduction in dietary nitrogen load. This is required as diseased kidneys are operating at 20% to 50% of normal capacity. The maximum amount of nitrogen waste workloads must be removed from diet in order for patients' blood work to improve rapidly.

Other comorbid conditions are eliminated or reduced like acidosis/metabolic acidosis by increasing natural bicarbonate intake and reducing renal acid load. Oxidative stress is also addressed. In three transplant patients, the dosage of Prograf was reduced as health improved on the diet. This is very important as Prograf is considered nephrotoxic. Reducing prograf dosage as health improves should increase the useful life of transplanted kidneys. Cholesterol and blood pressure also improves. Other areas are harder to measure such as oxidative stress and AGE's, but we know these are factors that contribute to kidney disease progression, but they are harder to measure.

As the number of comorbid conditions decreases, mortality rates decrease as well. Every time a comorbid condition is successfully managed or treated, the patient's odds go up. Nutrition labels for these patients now look like this in recipes or diet guides. Dietary adjustments or therapies represent the least risk and are most beneficial in extending the useful life of kidneys and a patient's overall quality of life. This diet has been shown to produce measurable blood test changes in as little as three weeks, however we believe the full ninety-day trial is needed for full access dietary potential for slowing kidney disease progression.

The recommendation for dietary treatment is a full ninety days on the prescribed diet to evaluate blood tests with their physician. If improvements are verified by blood and urine, then diet is extended another ninety days and so on until measurable improvements stop. Each ninety-day period, small changes may be needed to optimize blood tests to the normal range. Improvements are still being recorded at the one-year mark by test patients. When measurable improvements stop and blood/urine tests are stable, the diet plan is locked in so that patients can continue to extend the life of their kidneys.

Solving multiple problems: The first issue to solve is a prescribed diet treating as many factors as possible. This diet achieves those goals, but the diet is still not safe for long term use without protein and vitamin supplementation to safely achieve RDA's. This is true for any reduced protein diet. The type and amount of protein or vitamin supplementation is as important as diet, but dietary intake must be calculated before other problems can be solved. The next issue is protein supplementation. Dietary protein intake must be calculated based on prescribed diet. Goal is to meet the RDA for essential amino acids and for vitamin/minerals when dietary and supplemental intake is calculated.

Component Two (C2): Low Nitrogen Protein Food Albutrix™

In order to meet the goal of the lowest nitrogen load and a limit of 4,800 mg nitrogen per day a new protein food had to be researched and designed. Amino acids do not reduce nitrogen load sufficiently and calcium based keto analogues require high levels of supplemental calcium intake creating unacceptable risks and go against current guidelines. The prescribed diet of 0.4 grams of protein per body weight falls short of the 0.8 grams of protein RDA. The shortfall of 0.4 grams per day must be addressed with the lowest possible nitrogen while not causing the patient to take undue risks by exceeding RDAs.

Alpha keto acids reduce supplementation nitrogen intake more than amino acids. The term "alpha keto acid" refers to an alpha keto-carboxylic acid form, or "keto-analog" of an essential amino acid (EAA) (e.g., histidine, isoleucine, leucine, lysine, methionine, phenylalanine, threonine, tryptophan, and valine) or non-essential amino acid (non-EAA) (e.g., tyrosine) formed by the amine group being substituted by a ketone. Keto acids or keto amino acid blends have distinct advantages over traditional dietary protein consumption and traditional amino acid supplements. These benefits only apply to those patients with impaired amino acid or protein metabolism. In most cases, this impairment is related to handling protein metabolic products kidney, liver, aging, inflammation or microinflammation, metabolic acidosis, oxidative stress or related diseases.

After considering the different forms of keto analogues salt, aluminum, lithium, sodium, calcium, potassium, magnesium, etc., only magnesium has been shown to reduce mortality rates in kidney disease patients. All others represent toxic or high-risk dosages.

Magnesium based keto analogues have never been produced, manufactured or developed. The three largest producers of calcium based keto analogues were approached in Germany and China. All three manufacturers said magnesium based keto analogs were not possible and if they were possible it would take months of research and development to determine if scale manufacturing was possible or cost effective and if they could be made to meet pharmaceutical standards. Next, active pharmaceutical ingredient manufacturers (API) were approached in the US, Canada and India. After researching the subject, all companies came back with the same answer: No known method exists for the requested materials. The API companies could not manufacture unless a known manufacturing method existed. All three producers of keto analogues and seven API companies all came to the same conclusion. Magnesium based keto analogue could not be or had never been produced; so, no known method could be found for manufacture at any scale.

In order to find a way to produce magnesium salts as keto acids or alpha keto analogues, a new, novel conversion method was needed to convert existing supplies of keto analogues as calcium salts to magnesium salts. The inventor spent over 150 days testing different combinations and procedures to attain the desired results. No written documentation existed and no expert or company with decades of experience in producing keto analogues was able to produce the desired end product. The resulting manufacturing methods meet pharmaceutical standards and represent new treatment opportunities for stage 3, 4A and 4B patients. This research and development was done for valine, isoleucine, leucine, tyrosine and tryptophan—see US publication 20200281881 A1 by the present inventors. A second round of research and developed methionine and phenylalanine as magnesium salts—see Appendix A. The manufacturing methods contained here yield the lowest amounts of magnesium possible.

Problems included a methionine conversion process producing a "jelly" like substance that could not be dried properly using traditional methods. Other problems included low yields when the "jelly" problem was solved, impurity removal leading to 97% to 98% pure materials and yield was so low production could not be justified. Phenylalanine problems of persistent impurities existed through all traditional stages and known methods. New production techniques were required to remove impurities to produce a food and pharmaceutical grade product. All of these production problems encountered have been solved by the production methods of the present invention. No known documented procedures were used, could be found or discovered to solve this problem to produce a food and pharmaceutical grade product.

The end products of methionine and phenylalanine as alpha keto analogues of magnesium salt with 0% calcium content allow kidney patients to control both magnesium and calcium intake for the first time when using alpha keto analogues for a source of low nitrogen protein nutrition.

Figure 2:
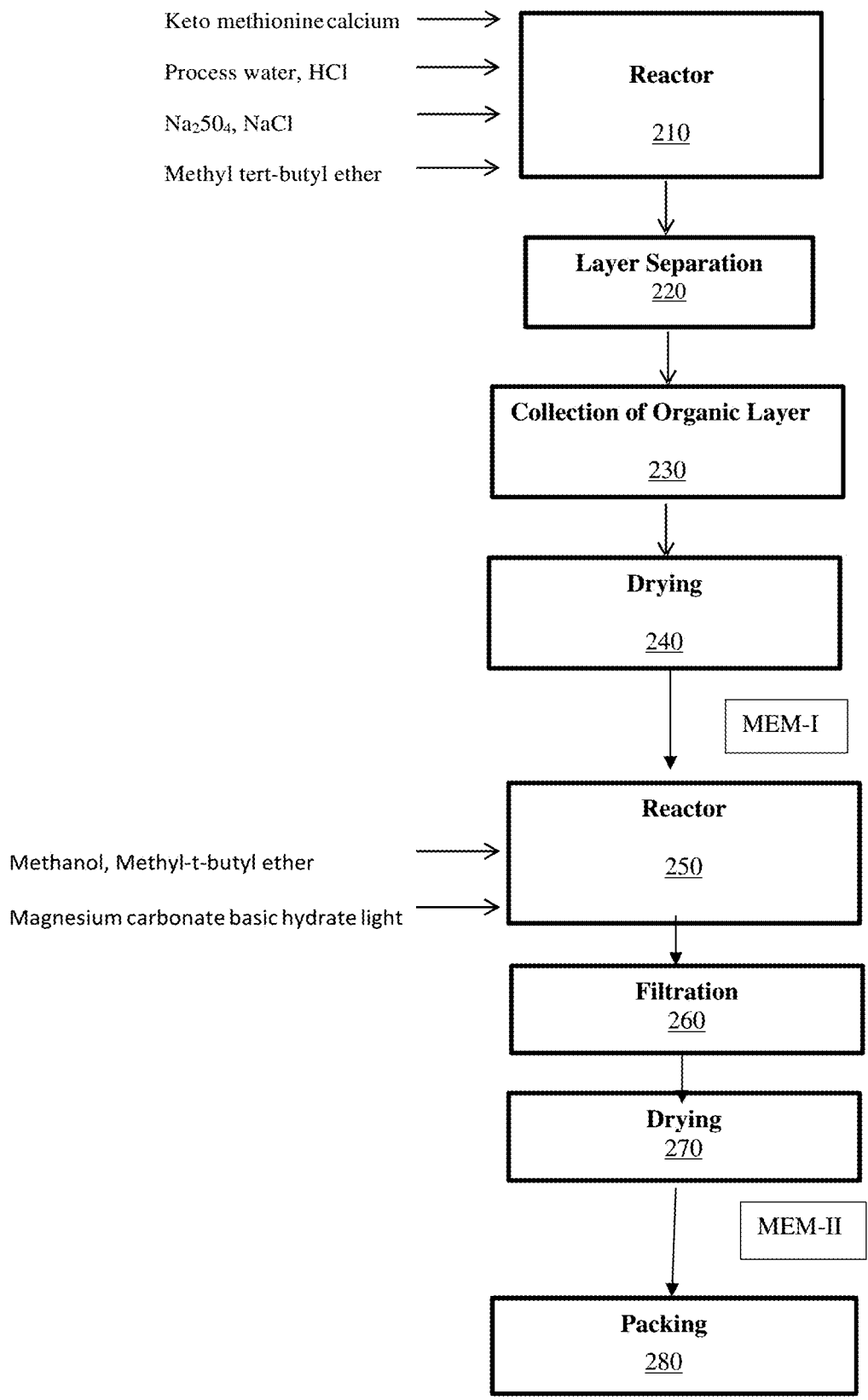
FIG. 2 is a flowchart steps in the two-stage process of producing a keto acid of methionine as magnesium salt (MEMS II) of FIG. 1.

Chemical Structures and Methods of Making MEMS II are listed in FIGS. 1 and 2 and the Appendix A. As illustrated in FIG. 1 and the flowchart of FIG. 2, the method of making MEMS-II comprises a multi-step process to first produce 4-(methylthio)-2-oxobutanoic acid (MEM-I), and then producing alpha keto methionine magnesium (MEM-II). In step 210, keto methionine calcium, process water, concentrated hydrogen chloride, and methyl tert-butyl ether are added to the reactor. Then the following steps are performed in Stage I: layer separation, step 220; collection of organic layer, step 230; and drying of the product MEM-I, step 240. And then the following steps are performed in Stage II: adding methanol, magnesium carbonate basic hydrate, and methyl-tert-butyl ether to MEM-I, step 250; filtrating, step 260; drying, step 270; and packaging, step 280. Specific details for each step are listed in Appendix A.

Figure 3:
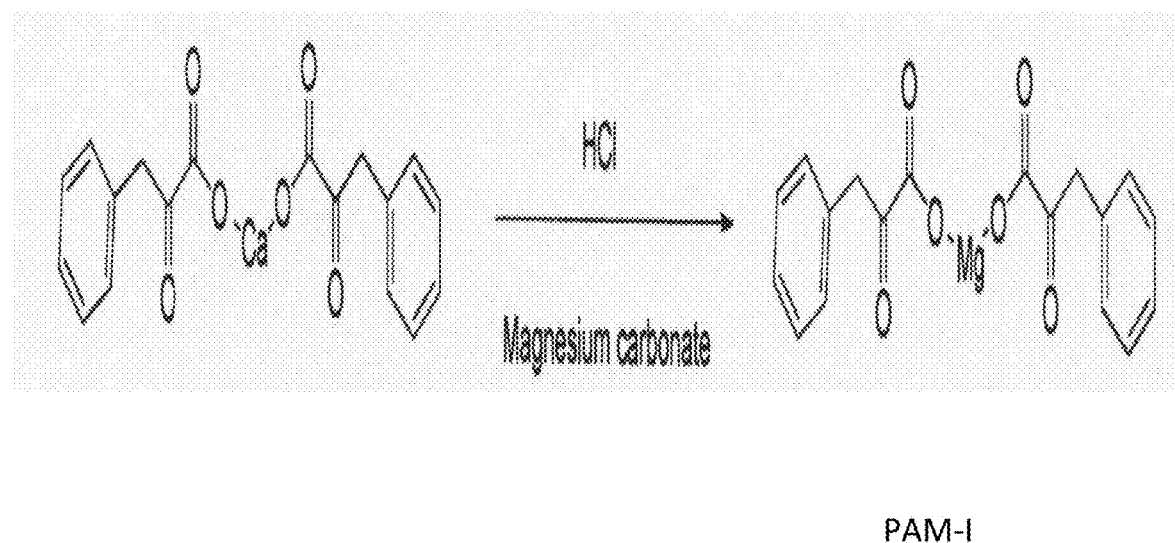
FIG. 3 is an illustration of the chemical structures in the route of synthesis for a keto acid of phenylalanine salt as a magnesium salt (PAM).
Figure 5:
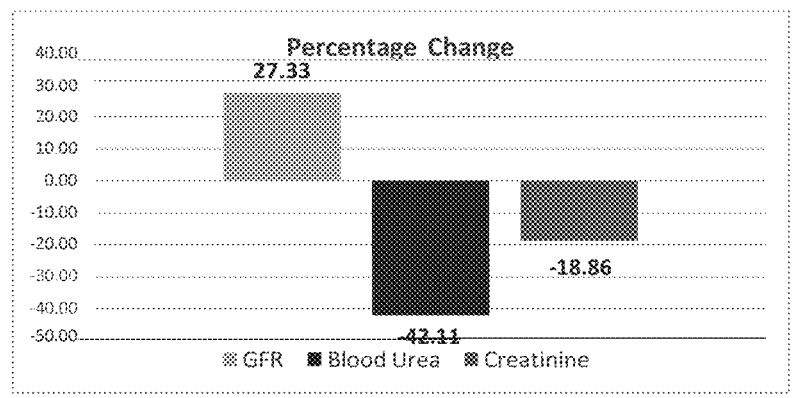
FIG. 5 is a bar graph illustrating the success in the formulations of Albutrix™ in treating patients with kidney disease in the clinical trial of FIG. 4.
Figure 6:
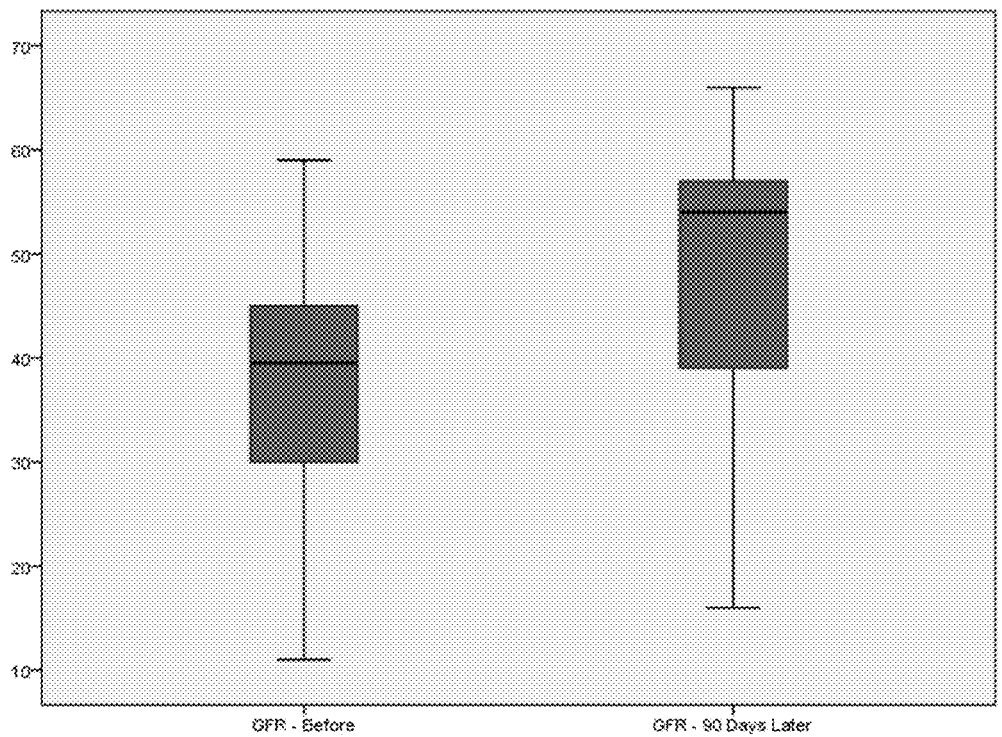
FIG. 6 is a bar graph illustrating the change in GFR before and 90 days after treatment from FIG. 4.
Figure 7:
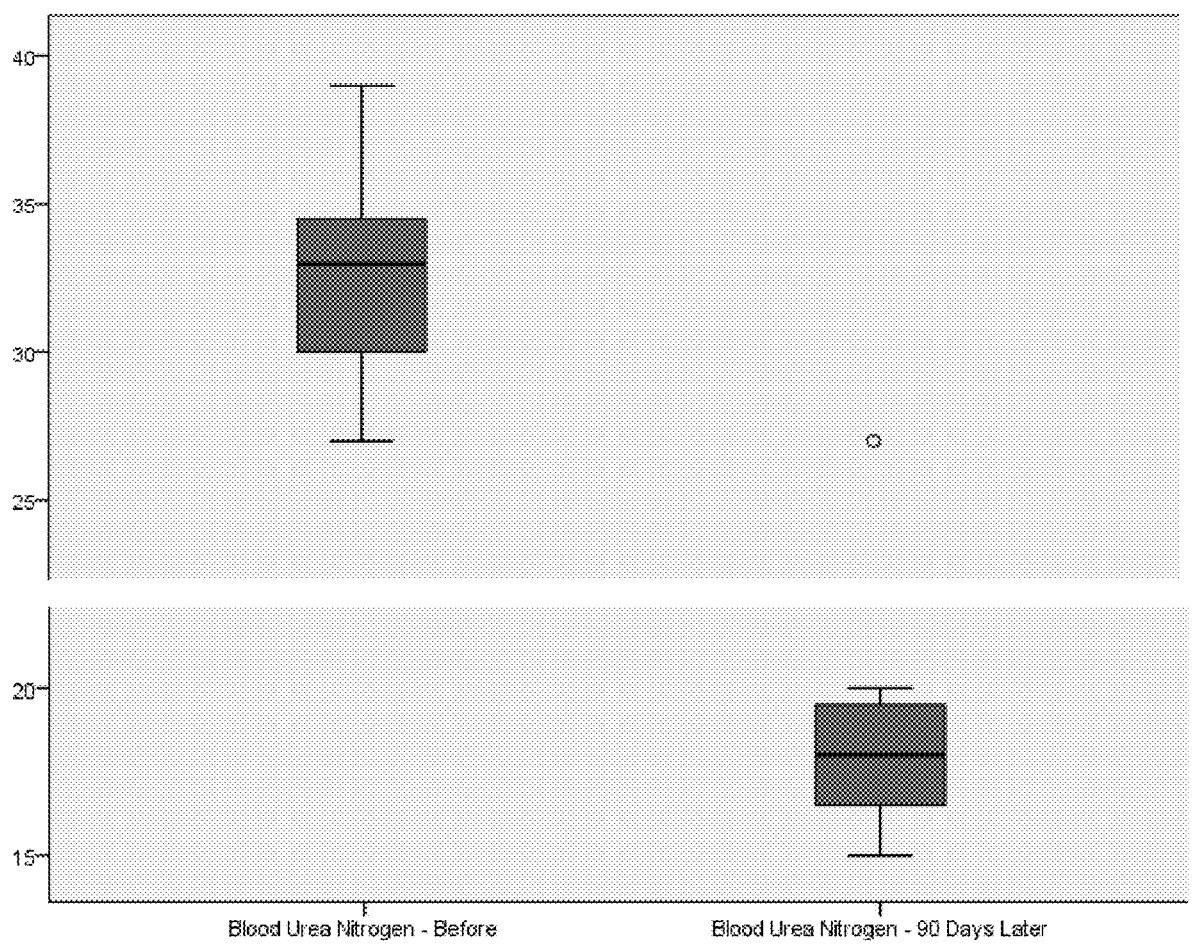
FIG. 7 is a bar graph illustrating the change in Blood Urea Nitrogen (BUN) before and 90 days after treatment from FIG. 4.
Figure 8:
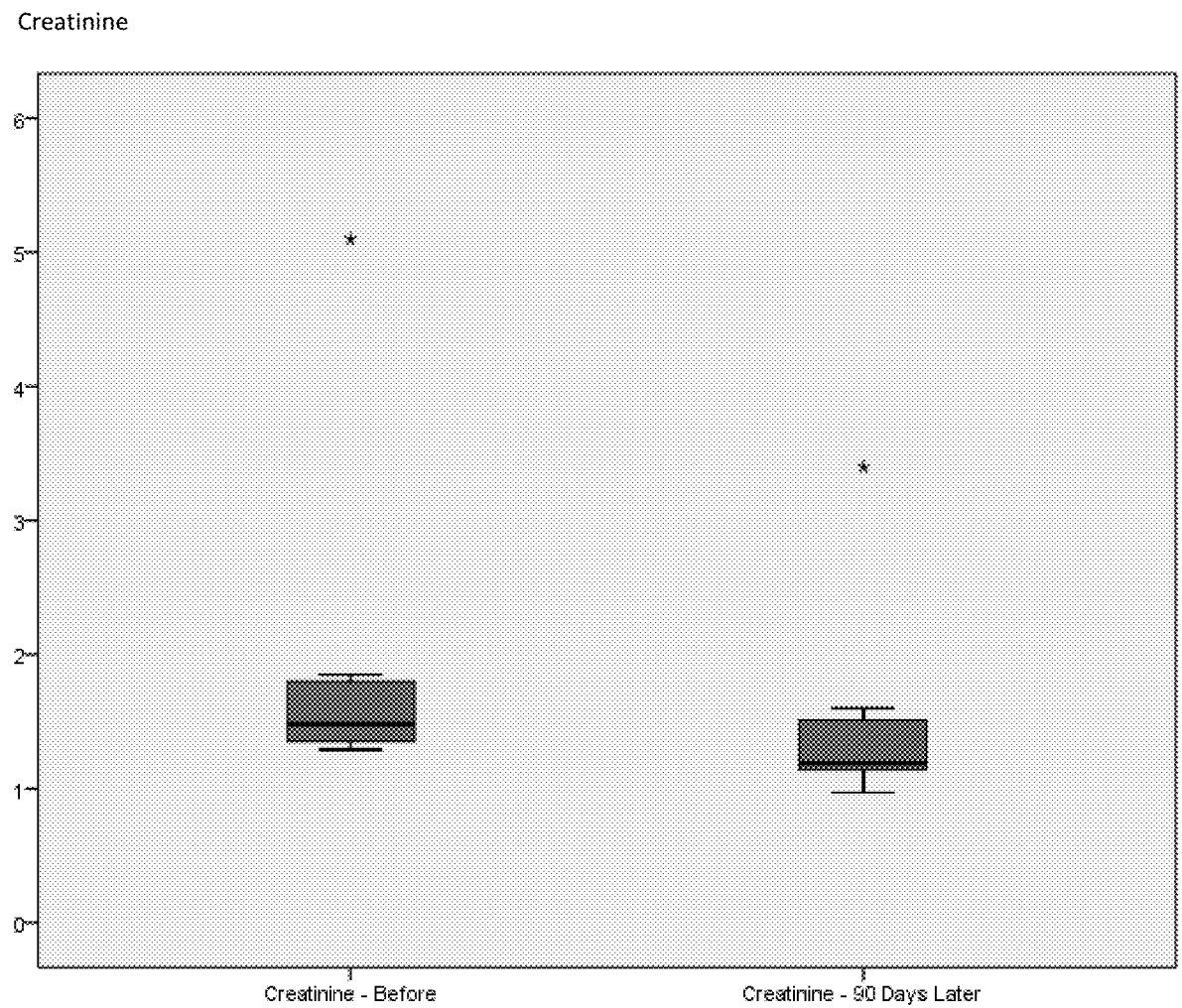
FIG. 8 is a bar graph illustrating the change in Creatine before and 90 days after treatment from FIG. 4.

Chemical Structures and Methods of Making PAMS are listed in FIG. 3 and in Appendix A, and comprise combining: keto phenylalanine calcium salt; process water; hydrochloric acid; methyl-t-butyl ether; magnesium carbonate hydrated basic light; and acetone.

The development of a manufacturing method for magnesium based keto analogues allows stage 3, 4A and 4B patients safe long-term use. In contrast, calcium based keto analogues are limited by over 30 countries to a GFR of 15 or 20 for safety reasons. This is the first time a safe, long term treatment has existed for stage 3-5.

For the prescribed diet, the essential amino acid intake per day was 8.97 grams for vegetarian diets that allowed eggs. For vegan diets, the essential amino acid intake was 5.03 grams per day, no eggs. The average of 7 grams of essential amino acids for the two diets.

It was found that several essential amino acids were supplied close to 100% of the recommended amounts by the prescribed kidney diet. No supplementation of tryptophan, histidine and phenylalanine were needed to reach 100% of the recommended amounts without supplementation. All past formulations include large amounts of histidine, phenylalanine, tryptophan and others with no benefit to the patient.

| Vegetarian low protein diet with eggs | |
|---|---|
| Essential Amino acid | Shortfall as a percentage of recommended daily amount |
| Histidine | +5.00% |
| Isoleucine | −37.93% |
| Leucine | −37.07% |
| Lysine | −44.43% |

| Vegetarian low protein diet with eggs | |
|---|---|
| Essential Amino acid | Shortfall as a percentage of recommended daily amount |
| methionine | −40.29% |
| Phenylalanine (no tyrosine) | +4.39% |
| Threonine | −18.57% |
| Tryptophan | +2.86% |
| Valine | −32.47% |

| Vegan or vegetarian no eggs allowed | |
|---|---|
| Essential Amino acid | Shortfall as a percentage of recommended daily amount |
| Histidine | −5.29% |
| Isoleucine | −49.93% |
| Leucine | −50.37% |
| Lysine | −57.33% |
| methionine | −56.71% |
| Phenylalanine (no tyrosine) | −15.41% |
| Threonine | −32.38% |
| Tryptophan | −9.80% |
| Valine | −44.18% |

Providing a large amount of essential amino acid has no known benefit to patients, only risks. These risks of large doses when diet and supplemental protein is factored in are not trivial.

Tryptophan recommended daily amounts are met with one diet and within 10% using the second vegan diet. However, Tryptophan is provided in other formulations from 500 to 912 mg. Tryptophan intake is associated with the tryptophan-derived uremic toxins (TDUT). These toxins are associated with accelerated heart and kidney disease. For a kidney patient intake of 190% to 200% of the recommended daily amount poses no benefits, only risks of accelerated heart and kidney disease progression.

Histidine has the highest nitrogen content of any essential amino acid at 27% nitrogen content. 95% to 100% is provided by dietary intake in the prescribed diet. Histidine is supplemented at rates from 500 to 800 mg in past formulations. This practice adds a large amount of nitrogen workload with no benefit to the patient, only risks.

Tyrosine is also a problem. Tyrosine intake is associated with uremic toxins p cresol sulfate. Tyrosine is not indicated in stage 3 and supplemental tyrosine only increases risk. Small amounts of tyrosine are used in stage 4A and a slightly increased amount in 4B.

Methionine is another problematic amino acid. Methionine is a precursor for homocysteine. Excess methionine intake increases homocysteine levels. Excess methionine has well known atherogenic properties. This is problematic as heart disease is the number one killer of kidney patients.

These are a few examples of the risks posed by excess intake after dietary intake is factored in. It also shows one of the reasons past approaches have failed.

In order to lower nitrogen intake to the lowest possible safe level while supplying 100% of the recommended daily amount, a new formulation is needed. Table 3 lists 100% of recommended daily amount is supplied, but based on actual dietary intake when used with a prescribed diet as disclosed herein to slow kidney disease progression.

TABLE 3

| | Percent of recommended daily amount need to achieve RDA |
|---|---|
| Histidine | 0.14% |
| Isoleucine | 43.93% |
| Leucine | 43.72% |
| Lysine | 50.88% |
| methionine | 48.50% |
| Phenylalanine (no tyrosine) | 5.51% |
| Threonine | 25.48% |
| Tryptophan | 3.47% |
| Valine | 38.32% |

Nitrogen content will vary based on formulation, this example shows how the combination of a low nitrogen prescribed diet with a prescribed keto analogue/amino acid protein food can reduce nitrogen load by 50% to 80% compared to amino acids or previous keto analogues/amino acids blends. This drastic reduction is needed to affect a patient's blood work meaningfully.

While hundreds of combinations of a prescribed protein food or keto analog/amino acid blend are possible, the prescribed protein food of the present invention (Albutrix™) must contain the following:

1. Supplemental nitrogen content less than 300 mg per day for average daily dose. Supplemental nitrogen intake higher than 500 mg should be avoided.
2. Supplemental calcium content less than 400 mg per day to allow safe dietary calcium intake without exceeded 1,200 mg per day for stage 4 and 4A. No calcium for stage 3 patients.
3. Supplemental magnesium content less than 220 mg per day for stage 4A, less than 120 mg for 4B, less than 350 mg per day for Stage 3.
4. Amino and keto analogues formation must be matched to prescribed diets to supply RDA's of essential amino acids and not more.
5. A different formulation for each stage of kidney disease treated Stage 3, 4A, 4B, and 5 is required to maximize nutrition and reduce risks and kidney workload.

Past amino acid or keto analogues/amino acids blends assume no dietary intake of amino acids. The recommendation has always been 100% of the RDAs regardless of dietary intake. This is another reason these diets fail to produce the desired result. This results in 200% or more of the RDA's in many cases as there is no prescribed diet to go with the protein food. This results in greatly increased nitrogen load with no known benefit.

The combination of low nitrogen plant-based diet matched with dietary shortfalls of essential acids combined with magnesium or magnesium/calcium blends that allow for dietary intake to match RDA's. The risks of excess calcium, magnesium, nitrogen and amino acid intake are all addressed by this approach. This approach represents the lowest possible risk to kidney patients and the lowest kidney workload. Nitrogen workload is reduced dramatically by this combined approach.

Prescribed dosage was greatly simplified to one pill that equals approximately 5 grams of dietary protein for planning purposes. While amino acid content for every food varies, this calculation is much easier for patients and is proportional for body weight and expected dietary intake. This allows patients to easily calculate needed dosage using the 0.8 grams per kg of protein recommendation. If 30 grams of supplemental protein is needed, the dosage is six pills per day. 25 grams of protein equals 5 pills and so on. Pill and keto analogue/amino acid content was increased to reduce the number of pills per day and simplify dosage instructions. While two major problems have been solved such as a prescribed diet treating/managing comorbid conditions that speed or slow kidney disease progression with the lowest possible nitrogen intake combined with a matched amino/keto analogues blends that keeps total intake from diet and supplement intake at safe levels at or below the RDA's while further reducing nitrogen levels.

The food as pills of the present invention are an improvement on the formulations disclosed in U.S. patent application Ser. No. 16/768,230 filed on May 29, 2020 (US20200281881 published on Sep. 10, 2020), which is a national stage application of PCT/US18/63086 filed on Nov. 29, 2018 by Edgar L. Hull et al., and who is the same inventorship as herein. The entire contents of this application are hereby incorporated herein by reference in its entirety. Specifically, the methionine (in S3 and S4a) and phenylalanine (in S3) alpha keto acids used within the compositions of the present invention comprise magnesium in lieu of calcium. Procedures for making valine, leucine and isoleucine magnesium alpha keto acids are as previously disclosed in US20200281881 Procedures for making methionine and phenylalanine magnesium alpha keto acids are disclosed herein (e.g. Appendix A).

The treatment program of the present invention further comprises daily administering one of the Albutrix™ compositions of Tables 4-7, which comprise four exemplary formulations of low nitrogen protein food that is pharmaceutical grade. These compositions are used to correctly supply protein nutrition, increase albumin levels and manage magnesium and calcium levels for each stage of kidney disease and current patient health while reducing the risk of vascular calcification/heart disease. The formulations used allow exact dosing and management of these conditions during different phases or stages of kidney disease progression. That for each listed value of milligrams/day listed in Tables 3-6 infra, these values can vary by in an embodiment+/−5%, and in another embodiment+/−10%; and this is the total intake per day, versus the amount in each tablet.

Also listed amounts in the tables are the required amounts of supplemental magnesium, calcium, and nitrogen required to be taken by the patient daily in the form of Albutrix™ S3, S4, S4a, S4b or S5 depending on stage of kidney disease.

ALBUTRIX S3™ in Table 4 comprises a formula comprising 100% magnesium and no calcium salts and no tyrosine, and that does require patients to exceed their recommended daily intake of magnesium. The target patient is a Stage 3 patient who can still safely tolerate a variety of magnesium intake levels.

TABLE 4

ALBUTRIX S3 ™

| Active Ingredients | Milligrams (mg)/day for protein nutrition | AA/KA per pill | % wt./wt. |
|---|---|---|---|
| Mg salt α keto analog of isoleucine | 742.00 | 123.67 | 14.95 |
| Mg salt α keto analog of leucine | 1439.48 | 239.91 | 28.99 |
| Mg salt α keto analog of hydroxy methionine (MEM-II) | 413.40 | 68.90 | 8.33 |
| Mg salt α keto analog of phenylalanine (PAM) | 64.98 | 10.83 | 1.31 |

TABLE 4-continued

ALBUTRIX S3 ™

| Active Ingredients | Milligrams (mg)/day for protein nutrition | AA/KA per pill | % wt./wt. |
|---|---|---|---|
| Mg salt α keto analog of valine | 799.24 | 133.21 | 16.10 |
| Histidine amino acid | 12.46 | 2.08 | 0.25 |
| L-lysine acetate | 1178.72 | 196.45 | 23.74 |
| L-threonine | 305.28 | 50.88 | 6.15 |
| Tryptophan amino acid | 9.43 | 1.57 | 0.19 |
| DAILY INTAKE TOTAL | 4964.99 | 827.50 | |
| Supplemental Magnesium = 297 mg | | | |
| Supplemental Calcium = 0 mg | | | |
| Supplemental Nitrogen = 200.63 mg | | | |

The amount of supplemental magnesium, calcium and nitrogen listed in the Albutrix™ Tables 4-7 are the amount consumed by the patient when taking 6 of the tablets per day.

The number of total Albutrix tablets taken per day is determined by RDA, which for dietary protein intake is 0.8 grams per kilogram of body weight. Each Albutrix™ tablet (i.e. the low nitrogen food) is roughly the equivalent to 5 grams of dietary protein. Amino acid content varies by food source, but for dietary planning the 5 gram equivalent works very well. The Kidney Factor diet recommends 0.4 grams of dietary protein per kg and 0.4 grams of equal dietary protein from Albutrix total intake. For example: a 75 kg adults would consume 60 grams of total protein per day to meet the 0.8 gram RDA, of which 30 grams are from dietary protein intake and six Albutrix pills to equal another 30 grams of dietary protein. Formulating Albutrix to the equivalent of 5 grams of dietary protein makes the calculation very easy for patients and caregivers to get the exact amount of protein needed with the lowest nitrogen load.

Combination of Magnesium and Calcium Salts

Tables 5 and 6 comprise compositions with a combination of magnesium and calcium salts of alpha keto analogues. The combination of magnesium and calcium reduces the possibility of exceeding RDAs. The combination of magnesium and calcium may be more effective, or as effective as, a phosphate binder than calcium salts alone. The combination is a safer way to reduce phosphorus than calcium alone.

ALBUTRIX S4a and S4 in Table 5 comprises a formula comprising magnesium and calcium salts in which calcium and magnesium amounts are appreciably equal, and target patients who are in a stage four kidney patient. In one embodiment, S4a can be used for all degrees of stage four, to include late stage 4 (S4). In another embodiment, S4b is used for late stage four.

TABLE 5

ALBUTRIX S4a and S4

| Active Ingredients | Milligrams/day for protein nutrition | AA/KA per pill | % wt./wt. |
|---|---|---|---|
| Mg salt α keto analog of leucine | 1405.00 | 234.17 | 28.37 |
| Mg salt α keto analog of methionine (MEMS II) | 404.92 | 67.49 | 8.18 |
| Mg salt α keto analog of valine | 300 | 50.00 | 6.057 |
| Ca salt α keto analog of isoleucine | 742.00 | 123.67 | 14.98 |
| Ca salt α keto analog of phenylalanine | 65.00 | 10.83 | 1.31 |

TABLE 5-continued

ALBUTRIX S4a and S4

| Active Ingredients | Milligrams/day for protein nutrition | AA/KA per pill | % wt./wt. |
|---|---|---|---|
| Ca salt a keto analog of valine | 500 | 83.33 | 10.09 |
| Histidine amino acid | 12.46 | 2.08 | 0.25 |
| L-lysine acetate | 1179.38 | 196.56 | 23.81 |
| L-threonine | 306.21 | 51.03 | 6.18 |
| Tryptophan amino acid | 9.46 | 1.58 | 0.19 |
| Tyrosine amino acid | 28.62 | 4.77 | 79.50 |
| DAILY INTAKE TOTAL | 4953.04 | 825.51 | |
| Supplemental Magnesium = 181 mg | | | |
| Supplemental Calcium = 181 mg | | | |
| Supplemental Nitrogen = 203.05 mg | | | |
| RDA for EAA's 100% w/diet | | | |

ALBUTRIX S4b™ in Table 6 comprises a formula comprising magnesium and calcium salts in which magnesium are lowered further and calcium is increased. This formulation was based on late stage 4 patients input.

TABLE 6

ALBUTRIX S4b ™

| Active Ingredients | Milligrams/day for protein nutrition | AA/KA per pill | % wt./wt. |
|---|---|---|---|
| Mg salt α keto analog of leucine | 1183.00 | 197.17 | 23.68 |
| Ca salt α keto analog of isoleucine | 739.88 | 123.31 | 14.81 |
| Ca salt α keto analog of leucine | 200.00 | 33.33 | 4.00 |
| Ca salt α keto analog of methionine | 457.92 | 76.32 | 9.17 |
| Ca salt α keto analog of phenylalanine | 65.00 | 10.83 | 1.31 |
| Ca salt α keto analog of valine | 799.24 | 133.21 | 16.00 |
| Histidine amino acid | 12.46 | 2.08 | 0.25 |
| L-lysine acetate | 1179.38 | 196.56 | 23.61 |
| L-threonine | 306.21 | 51.03 | 6.13 |
| Tryptophan amino acid | 9.46 | 1.58 | 0.19 |
| Tyrosine amino acid | 42.40 | 7.07 | 0.85 |
| DAILY INTAKE TOTAL | 4994.94 | 832.49 | |
| Supplemental Magnesium = 100 mg | | | |
| Supplemental Calcium = 306 mg | | | |
| Supplemental Nitrogen = 204.11 mg | | | |
| RDA for EAA's 100% w/diet | | | |

ALBUTRIX S5™ in Table 7 comprises a formula comprising no magnesium while comprising higher calcium salts levels for stage five or end stage renal disease patients who already have magnesium levels above the normal range or who cannot safely tolerate supplemental magnesium of any amount.

TABLE 7

ALBUTRIX S5 ™

| Active Ingredients | Milligrams/day for protein nutrition | AA/KA per pill | % wt./wt. |
|---|---|---|---|
| Ca salt α keto analog of isoleucine | 739.88 | 123.31 | 14.77 |
| Ca salt α keto analog of leucine | 1436.00 | 239.33 | 28.67 |
| Ca salt α keto analog of methionine | 404.92 | 67.49 | 8.09 |
| Ca salt α keto analog of phenylalanine | 65.00 | 10.83 | 1.30 |
| Ca salt α keto analog of valine | 799.24 | 133.21 | 16.00 |
| Histidine amino acid | 12.46 | 2.08 | 0.25 |
| L-lysine acetate | 1178.72 | 196.45 | 23.54 |

TABLE 7-continued

ALBUTRIX S5 ™

| Active Ingredients | Milligrams/day for protein nutrition | AA/KA per pill | % wt./wt. |
|---|---|---|---|
| L-threonine | 305.28 | 50.88 | 6.10 |
| Tryptophan amino acid | 9.46 | 1.58 | 0.19 |
| Tyrosine amino acid | 57.24 | 9.54 | 1.14 |
| DAILY INTAKE TOTAL | 5008.19 | 834.70 | |
| Supplemental Magnesium = 465 mg | | | |
| Supplemental Calcium = 0 mg | | | |
| Supplemental Nitrogen = 204.57 mg | | | |
| RDA for EAA's 100% w/diet | | | |

The compounds of the present invention may be used in oral formulations (e.g. tablets, drinks-nutraceuticals, food, etc.), such as the pills of Tables 4-7 (ALBUTRIX™ S3, S4, S4a, 4b, and-S5). For example, the formulations may be used to treat Stage 3-5 kidney patients who are not deficient in calcium to do several things not available before:
1. Control/reduce calcium intake to stay below, at or just above the RDA.
2. Control/increase magnesium intake to stay below, at or just above the RDA.
3. Reduce, slow or stop vascular calcification.
4. Reduce inflammation.
5. Reduce the risk of kidney stones.
6. Reduce the risk of cardiovascular events.
7. Change calcium or magnesium intake as needed if current health warrants a change.
8. Increase albumin levels. Much of albumin is bound to magnesium. Low magnesium levels correlate with low albumin numbers.
9. Reduce phosphorus levels without increasing calcium intake.
10. A safe alternative for early intervention or treatment before stage 5 or before GFR falls below 25, 20 or 15. Calcium intake is not indicated for GFR above 25, 20 or 15 in almost all cases.
11. Magnesium levels are inversely correlated with survival rates in kidney disease patients. Patients with the highest magnesium levels have the highest survival rates.

Component Three (C3): Vitamin Composition

Table 8 lists the active ingredients in an exemplary version of the vitamin composition of the present invention, in which each tablet or pill comprises: Zinc; Selenium; Vitamin B1-Thiamine; B2-Riboflavin; Niacin; B6 Pyridoxine HCl; Folate as Folic Acid; Vitamin B12; Vitamin B5; Vitamin E; and Vitamin K2.

In another exemplary embodiment, each tablet or pill consists of the active ingredients and amounts as listed in Table 7.

TABLE 8

| Vitamin | | |
|---|---|---|
| Active Ingredients | Amount per serving/pill | % Daily Value |
| Zinc (as zinc bisglycinate chelate) | 8.50 mg | 75% |
| Selenium (as selenium methionine) | 50.00 mcg | 90% |
| Vitamin B1 (as thiamine mononitrate) | 0.23 mg | 20% |
| Vitamin B2 (as Riboflavin) | 0.10 mg | 8% |
| Niacin (as niacinamide) | 7.00 mg | 45% |
| Vitamin B6 (as pyridoxine HCl) | 0.25 mg | 15% |

TABLE 8-continued

| Vitamin | | |
|---|---|---|
| Active Ingredients | Amount per serving/pill | % Daily Value |
| Folate (as folic acid) | 85.00 mcg | 20% |
| Vitamin B12 (as methylcobalamin) | 2.20 mcg | 90% |
| Vitamin B5 (as pantothenic acid) | 1.70 mg | 35% |
| Vitamin E (as d-alpha-tocopherol succinate) | 3.50 mg | 25% |
| Vitamin K2 (as menaquinone-4) | 45.00 mcg | |

In one or more embodiments, the vitamin further comprises one or more of: liposomal, reduced or oxidized glutathione or S-Acetyl Glutathione (GSH) (e.g. about 670.0 mg); liposomal or lecithinized superoxide dismutase (SOD) (e.g. about 33.0 mg); and liposomal or lecithinized catalase (CAT) (e.g. about 245.0 mg).

The vitamin composition of the present invention does not comprise: calcium (Ca); magnesium (Mg); phosphorus (P); sodium (Na); manganese (Mn); fluoride (F); Vitamin D; and Vitamin K1.

In an exemplary embodiment, the vitamin composition further comprises, or consists of, the inactive ingredients of: calcium carbonate, microcrystalline cellulose, hydroxypropyl methylcellulose, stearic acid, magnesium stearate, and silica.

In an embodiment, the vitamin is formulated in a time release pill or tablet or capsule by methods well known in the art. For example, hydroxypropyl methylcellulose is used as a pharmaceutical adjunct which provides a sustained release of the active constituents of the tablet. Based upon the physical parameters involved in formation of a tablet which is determined by the nature of the ingredients (compressibility, adhesion of particles, etc.), up to 20% of the dry weight could be required for hydroxypropyl methylcellulose to ensure proper time release. Thus, according to one embodiment, a total formulation weight, including time released material, would have a weight of about 1.15 g/tablet. Because of the bulk of the formulation, the formulation is preferably produced and administered as 1 tablet per day.

To support the treatment plans and to support the most beneficial nutrient consumption, the present invention comprises a time-release low dose vitamin based on an analysis of kidney patient dietary intake, a prescribed diet and current RDA recommendations. Indeed, without an understanding of the amounts of specific nutrients that kidney disease patients are consuming, it is impossible to formulate an effective vitamin or supplement.

To determine the optimal formulation for a vitamin, the present invention analyzed kidney disease patients' intake of the following substances: Protein, nitrogen, antioxidants (ORAC), Potential renal acid load (PRAL), dietary fiber, polyphenols, potassium, phosphorus, sodium, calcium, iron, nitrates, magnesium, zinc, copper, manganese, selenium, fluoride, cholesterol, total phytosterols, Campesterol, Stigmasterol, Beta-sitosterol, Thiamin(B-1), Riboflavin(B-2), Niacin(b-3), vitamin B-6, B12, folate, Pantothenic Acid (mg), vitamin A, C, D, E, K, retinol, alpha carotene, beta carotene, Beta Cryptoxanthin, Lutein+Zeaxanthin, lycopene, isoleucine, leucine, valine, methionine, cysteine, phenylalanine, lysine, histidine, tryptophan, tyrosine, threonine, melatonin, glutathione and Nicotinamide adenine dinucleotide (NAD+).

These data enabled the present inventive entity to develop a vitamin that overcomes the limitations of scattershot approaches to nutrition that have conventionally been used by kidney disease patients and that have led to inadequate results and may yield bad outcomes. When used with a prescribed or known diet, this vitamin can provide a safe way to ensure proper nutrition in kidney disease patients who are lowering protein intake to reduce the workload on their kidneys.

Benefits

This micronutrient vitamin will provide 85% to 115% of RDA when diet and supplementation are added together. This approach is critical to balance the different risks that contribute to the acceleration of kidney disease progression. While nutrient deficiencies can adversely impact common comorbid conditions, overconsumption can also tax the kidneys unnecessarily. Through this approach, patients will benefit from the following as listed:

No micronutrient malnutrition
No protein malnutrition
No increase in kidney disease progression due to high dose vitamins
No unnecessary risks with no benefits
No wasting money or time on ineffective or unnecessary supplements
No harmful side effects
Improved quality of life
Reduced mortality rates
Direct supplementation of primary antioxidants Vitamin K2 has no recommended daily amount; however, K2 is added to the vitamin. The prescribed diet is low in foods that contain K2, renal K2 is low in kidney patients and K2 intake is inversely proportional to vascular calcification the number one killer of kidney patients. Vitamin K1 is not supplemented as dietary intake is adequate. The goal is normalization of all levels but not one milligram more than is needed to meet the RDA after diet is taken into account.

This five component framework is tailored to diet, protein supplement, RDA shortfalls or excess and low dose time release, understanding of kidney patients excesses and shortfall and a high standard for evidence based medicine combined with direct supplementation allow early and aggressive intervention to slow kidney disease progression, reduce mortality rates and improve patients quality of life in a safe manner not available to patients before.

Ensuring malnutrition will never be an issue for kidney patients must have several components in place to ensure maximum nutrition with minimal risk and be a cornerstone to the long-term survival of kidney disease patients.

Vitamin and Food Coatings

The formulations in the compositions of the present disclosure may be administered orally in a pill or tablet form to improve patient compliance and control of dosage.

These solid oral compositions may be prepared by conventional methods of blending, filling, tableting or the like. Repeated blending operations may be used to distribute the active agents throughout those compositions employing large quantities of fillers. Such operations are, of course, conventional in the art.

The compositions of the present invention may further comprise an inactive ingredient selected from the group consisting of a carrier, a binder, an excipient, a dye, and combinations thereof.

Solid dosage forms for oral administration may include capsules, tablets, caplets, pills, troches, lozenges, powders, and granules. A capsule typically comprises a core material comprising a composition of the invention and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylenevinyl acetate copolymers; and shellac (purified lac). Some such polymers may also function as taste-masking agents.

Tablets, pills, and the like may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

Tablets for oral administration are usually presented in a unit dose, and contain conventional excipients such as binding agents, fillers, diluents, tableting agents, lubricants, disintegrants, colorants, flavorings, and wetting agents. The tablets may be coated according to well-known methods in the art.

Suitable fillers for use include, mannitol and other similar agents. Suitable disintegrants include starch derivatives such as sodium starch glycolate. Suitable lubricants include, for example, magnesium stearate.

EXEMPLIFICATIONS

Example 1- Clinical Trial

FIG. 4 is a table listing the results of a clinical trial of twelve Kidney disease patients in one of Stages 2-5 followed the Kidney Factor diet and used the appropriate Albutrix™ formulation for their stage of kidney disease. (ALBUTRIX™ S3, S4a, 4b, and S5). After 90 days of treatment, an increase of 27.33% in GFR, a decrease of BUN of 42.11%, and a decrease of Creatinine of 18.86% (see FIGS. 5-8). There was also lower Prograf doses for transplant patients and a reduction in the number of comorbid conditions. After a 28% increase in GFR, one year later GFR levels are still increased showing a slowing of disease progression. The combination of increasing GFR and maintaining the increased GFR long term work together to dramatically slow kidney disease progression in kidney disease and kidney transplant patients.

Example 2

Stage 3 Chronic Kidney Disease Reversed while on Stopping Kidney Disease Diet & Albutrix™

Here we discuss the experience of an active 75-year-old Caucasian physician with a medical history of high cholesterol, gout, kidney stones, and a heart attack, diagnosed with stage 3 chronic kidney disease (CKD) in his late sixties. While in the hospital for surgery to treat his heart condition in 2014, his lab results showed a cause for concern, as his kidneys were not functioning properly. During that hospital stay after treatment for his heart attack, an internal medicine doctor at the hospital noticed elevated Creatinine levels (FIG. 9). The doctor ordered a renal ultrasound, which showed increased echo genic activity (body tissue's ability to reflect sound waves). He suggested follow-up with a different nephrologist once his patient fully recovered from the heart procedure. However, still concerned that a history of gout might have affected the kidneys and that his patient might be on the wrong gout medication (Probenecid™), a nephrologist was consulted while at the hospital. After reviewing labs and assessing the patient's new state (the recent heart procedure could have contributed to the new kidney issues), no further tests were completed. Two stents were placed after the heart attack, and he did well, reporting no new no cardiac symptoms. After discharge, he was followed closely by a primary care doctor. A few months after his hospital stay, a kidney stone was removed. The urologist noted elevated protein in the urine, recommending a repeat kidney ultrasound and follow-up with a nephrologist. This time the renal labs were even more concerning, and the diagnosis was made with Creatinine of 1.61 mg/dL and eGFR 41 (mL/min/1.73 m$^2$).

He reports little to no alcohol intake. He exercises about 45 minutes per day at least five times per week, enjoying swimming, walking, and golf. Prior diagnostic studies on him included multiple prostate biopsies, which showed a high prostate-specific antigen (PSA). Those biopsies were negative, a total of three times. With his medical record painting an otherwise healthy profile for his age, the patient was still surprised about the diagnosis and sought a second opinion, which confirmed the diagnosis of stage 3 kidney disease.

Within a few months of starting the diet disclosed herein, and taking Albutrix™ S3, he noticed positive changes correlated with a downward trend in his kidney labs. At the risk of progressing to stage 4 chronic kidney disease, his Creatinine peaked at 2.0 mg/dL in January 2019. It dropped to 1.54 mg/dL in May, and by September of the same year, his Creatinine was 1.3 mg/dL. He not only stopped the progression but had somehow reversed the course of the disease, according to the labs and the way he felt. The patient reports compliance with the Stopping Kidney Disease diet and has been on it for 20 months with no complaints. See results as illustrated in the Kidney Lab Table infra.

TABLE 9

Kidney labs

| Labs | July 14 | October 17 | August 18 | November 18 | January 19 | February 19 | March 19 | May 19 | Septembet 19 | January 20 | June 20 |
| --- | --- | --- | --- | --- | --- | --- | --- | --- | --- | --- | --- |
| BUN | — | — | 31 | 36 | 33 | 33 | 34 | 29 | 20 | 21 | 25 |
| Creatinine | 1.61 | 1.66 | 1.58 | 1.85 | 1.96 | 2.00 | 1.90 | 1.54 | 1.30 | 1.43 | 1.26 |
| eGFR | 41 | 41 | 43 | 35 | 33 | 32 | 39 | 51 | 54 | 48 | 55 |

Conclusion

Other features that are considered as characteristic for the various embodiments are set forth in the appended claims.

Although the various embodiments are illustrated and described herein as embodied in nutritional compositions and food products, it is nevertheless not intended to be limited to the details shown, since various modifications and structural changes may be made therein without departing from the spirit of the invention and within the scope and range of equivalents of the claims.

The product names used in this document are for identification purposes only. All trademarks and registered trademarks are the property of their respective owners.

LIST OF REFERENCES CITED

[1] F. M. Iorember, "Malnutrition in Chronic Kidney Disease", Front Pediatr. Jun. 20, 2018; 6: 1-9.
[2] A. A. House et al., "Effect of B-Vitamin Therapy on Progression of Diabetic Nephropathy. A Randomized Controlled Trial", JAMA. Apr. 28, 2010; 303(16):1603-1609.
[3] G. Ruiz-Hurtado et al., "Development of albuminuria and enhancement of oxidative stress during chronic renin-angiotensin system suppression", J Hypertens. 2014 October; 32(10):2082-91.
[4] H. F. Tbahriti et al., "Effect of Different Stages of Chronic Kidney Disease and Renal Replacement Therapies on Oxidant-Antioxidant Balance in Uremic Patients", Biochemistry Research International, pages 1-9.
[5] B. A. Zachara et al., "Selenium and glutathione peroxidases in blood of patients with different stages of chronic renal failure", J Trace Elem Med Biol. 2004; 17(4):291-9. Abstract.

[6] E. E. van de Lagemaat, "Vitamin B12 in Relation to Oxidative Stress: A Systematic Review", Nutrients 2019, 11, 482.
[7] S. R. Lee, "Critical Role of Zinc as Either an Antioxidant or a Prooxidant in Cellular Systems", Hindawi Oxidative Medicine and Cellular Longevity, 2018, pages 1-12.
[8] G. E. Arteel, H. Sies, "The biochemistry of selenium and the glutathione system", Environ Toxicol Pharmacol. 2001 September; 10(4):153-8.

Appendix A—Method of Making MEMS-II & PAM

Manufacturing Process for Alpha Keto Analogue Methionine Magnesium

As illustrated in FIG. 1, the production of keto methionine magnesium (MEM-II) is a two-stage process. FIG. 2 is a flowchart of general steps that Stage I and II follow. Then the following steps are performed in Stage I to produce 4-(methylthio)-2-oxobutanoic acid (MEM-1). In step 210, keto methionine calcium, process water, concentrated hydrogen chloride, and methyl tert-butyl ether are added to the reactor. Then the following steps are performed in Stage I: layer separation (220); collection of organic layer (230); and drying of the product MEM-I (240). And then the following steps are performed in Stage II: adding methanol and magnesium carbonate basic hydrate to MEM-I (250); filtrating (260); drying (270); and packaging (280).

TABLE 11

Method of Making Procedure MEMS-I:

| | | | |
|---|---|---|---|
| 1 | | | Check the cleanliness of the round bottom flask |
| 2 | 100 | gm | Charge the keto methionine calcium salt |
| 3 | 400 | ml | Charge the process water |
| 4 | | | Stir the mass for 15 minutes |
| 5 | 52 | ml | Slowly add the hydrochloric acid to the mass till pH attains 1-2 |
| 6 | 100 | gm | Charge the sodium chloride |
| 7 | | | Stir for 15 minutes |
| 8 | 300 | ml | Charge Methyl-t-butyl ether to reaction mass |
| 9 | | | Stir for 15 minutes |
| 10 | | | Allow to separate two layers |
| 11 | | | Collect the top methyl-t-butyl ether separately |
| 12 | | | Charge back the aqueous layer to round bottom flask |
| 13 | 100 | ml | Add methyl-t-butyl ether to aqueous layer |
| 14 | | | Stir for 15 minutes |
| 15 | | | Allow to separate two layers |
| 16 | | | Collect the top methyl-t-butyl ether separately |
| 17 | | | Combine the organic layers |
| 18 | 25 | gm | Add sodium sulfate to organic layer |
| 19 | | | Allow the organic layer to stand for 15 minutes |
| 21 | | | Distill of the solvent completely under vacuum below 50° C. |
| 22 | 74.70 | gm | Yield of MEM-1 |

TABLE 12

Stage-11: Synthesis of alpha keto methionine magnesium (MEM-II) Materials:

| SI No | Raw material | MW | Quantity | UOM | Moles | MR | Make |
|---|---|---|---|---|---|---|---|
| 1 | MEM-1 | 148.18 | 74.70 | gm | 0.504 | 1 | In house |
| 2 | Magnesium carbonate Hydrated basic light $(MgCO_3)_4Mg(OH)_2 \cdot 5H_2O$ | 485.65 | 23.60 | gm | 0.048 | 0.096 | HR grade |
| 3 | Methanol | — | 1100 | ml | — | — | HR grade |
| 4 | Methyl-t-butyl ether | — | 100 | ml | — | — | HR grade |

TABLE 10

Stage-1: Synthesis of 4-(methylthio)-2-oxobutanoic acid (MEM-1) Materials:

| SI No | Raw material | MW | Quantity | UOM | Moles | MR | Make |
|---|---|---|---|---|---|---|---|
| 1 | Keto methionine calcium salt | 334.42 | 100 | gm | 0.299 | 1 | LR grade |
| 2 | Process water | — | 400 | ml | — | — | In house |
| 3 | Hydrochloric acid | 36.46 | 52 | ml | — | — | HR grade |
| 4 | Sodium chloride | 58.44 | 100 | gm | — | — | HR grade |
| 5 | Methyl-t-butyl ether | — | 500 | ml | — | — | HR grade |
| 6 | Sodium sulfate anhydrous | 142.04 | 25 | gm | — | — | HR grade |

TABLE 13

Method of Making Procedure MEM-II:

| SI No | Quantity | UOM | Procedure |
|---|---|---|---|
| 1 | | | Check the cleanliness of the round bottom flask |
| 2 | 74.70 | gm | Charge the MEM-1 |
| 3 | 1100 | ml | Charge the methanol |
| 4 | | | Stir the mass for 15 minutes |
| 5 | 23.60 | gm | Charge the magnesium carbonate hydrated basic light |
| 6 | | | Heat the mass at 60-65° C. for 14 hours with stirring |
| 7 | | | Cool the mass to room temperature |
| 8 | | | Filter the precipitated solid |
| 9 | 100 | ml | Wash the material with methyl-t-butyl ether |
| 10 | 71.00 | gm | Dry the product to constant weight at 60° C. (MEM-II) |

Manufacturing Process for Keto Phenylalanine Magnesium

FIG. 3 is an illustration for the chemical structures in the route of administration of alpha keto analogue of phenylalanine magnesium.

TABLE 14

Raw materials-Components, Ingredients:

| SI No | Raw material | MW | Quantity | UOM | Moles | MR | Make |
|---|---|---|---|---|---|---|---|
| 1 | Keto phenylalanine calcium salt | 366.38 | 100 | gm | 0.272 | 1.00 | LR grade |
| 2 | Process water | — | 1000 | ml | — | — | In house |
| 3 | Hydrochloric acid | 36.46 | 70 | ml | — | — | LR grade |
| 4 | Methyl-t-butyl ether | — | 500 | ml | — | — | LR grade |
| 5 | Magnesium carbonate Hydrated basic light $(MgCO_3)_4Mg(OH)_2 \cdot 5H_2O$ | 485.65 | 22.91 | gm | 0.047 | 0.172 | LR grade |
| 6 | Acetone | — | 200 | ml | — | — | LR grade |

TABLE 15

Method of Making PAM-I:

| SI No | Quantity | UOM | Procedure |
|---|---|---|---|
| 1 | | | Check the cleanliness of the round bottom flask |
| 2 | 100 | gm | Charge the keto phenylalanine calcium salt |
| 3 | 500 | ml | Charge the process water |
| 4 | | | Stir the mass for 15 minutes |
| 5 | 70 | ml | Slowly add the hydrochloric acid to the mass till pH attains 1-2 |
| 7 | 300 | ml | Charge methyl-t-butyl ether to reaction mass |
| 8 | | | Stir for 15 minutes |
| 9 | | | Allow to separate two layers |
| 10 | | | Collect the top methyl-t-butyl ether separately |
| 11 | | | Charge back the aqueous layer to round bottom flask |
| 12 | 100 | ml | Add methyl-t-butyl ether to aqueous layer |
| 13 | | | Stir for 15 minutes |
| 14 | | | Allow to separate two layers |
| 15 | | | Collect the top methyl-t-butyl ether separately |
| 16 | | | Charge back the aqueous layer to round bottom flask |
| 17 | 100 | ml | Add methyl-t-butyl ether to aqueous layer |
| 18 | | | Stir for 15 minutes |
| 19 | | | Allow to separate two layers |
| 20 | | | Collect the top methyl-t-butyl ether separately |
| 21 | | | Combine the organic layers |
| 22 | | | Check the cleanliness of round bottom flask |
| 23 | | | Charge the combined organic layer to round bottom flask |
| 24 | 500 | ml | Charge process water |
| 25 | 22.91 | gm | Charge Magnesium carbonate hydrated basic light |
| 26 | | | Heat the mass at 60-65° C. for 5 hours with stirring |
| 27 | | | Cool the mass to room temperature |
| 28 | | | Filter the mass |
| 29 | | | Collect the filtrate |
| 30 | | | Separate the organic and aqueous layer of filtrate |
| 31 | | | Collect the aqueous layer |
| 32 | | | Concentrate the aqueous layer at 60° C. to constant weight |
| 33 | | | Collect the precipitated solid |
| 34 | | | Check the cleanliness of round bottom flask |
| 35 | 70 | gm | Charge the solid to round bottom flask |
| 36 | 100 | ml | Charge the acetone |
| 37 | | | Stir vigorously for 15 minutes |
| 38 | | | Filter the mass |
| 39 | | | Dry the material at room temperature |
| 40 | 60 | gm | Charge back the solid to round bottom flask |
| 41 | 100 | ml | Charge the acetone |
| 42 | | | Stir vigorously for 15 minutes |
| 43 | | | Filter the mass |
| 44 | 50 | gm | Dry the product at 60° C. to constant weight (PAM-I) |

TABLE 15

CERTIFICATE OF ANALYSIS

Product Name: Alpha keto phenylalanine magnesium Structure

Mol. Formula: $C_{18}H_{16}MgO_6$
Mol. Weight: 350.61
Batch Number: SCP-PAMA-03
Date of Synthesis: 14th Aug. 2019
Date of Analysis: 15th Aug. 2019

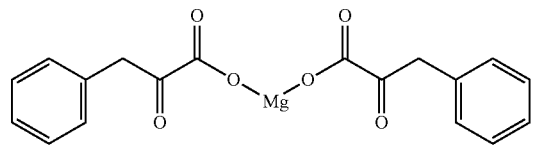

TABLE 15-continued

CERTIFICATE OF ANALYSIS

| Sl. No | Test | Specification | Result |
|---|---|---|---|
| 1 | Appearance | White sold | White solid |
| 3 | Solubility | Soluble in water | Soluble in water |
| 2 | Moisture content | Not more than 10% | 9.84% |
| 4 | Magnesiuns content (Anhydrous basis) | 6.23% to 7.62% (90% to 110%) | 6.89% |
| 5 | HPLC Purity | Not less than 90% | 91.70% |

Remarks:
The material complies with the specifications

What is claimed is:

1. A vitamin composition for use in a safe and low risk malnutrition treatment while slowing kidney disease progression in Chronic Kidney Disease Patients, comprising:
   i) active ingredients consisting of: Zinc; Selenium; Vitamin B1; Vitamin B2; Niacin; Vitamin B6; Folate; Vitamin B12; Vitamin B5; Vitamin E; Vitamin K2; glutathione (GSH); superoxide disumtase (SOD); and catalase (CAT); and
   ii) excluding all of the following: calcium (Ca); magnesium (Mg); phosphorus (P); sodium (Na); manganese (Mn); fluoride (F); Vitamin D; and Vitamin K1;
   iii) a non-naturally occurring inactive ingredient comprising one or more of: microcrystalline cellulose, and hydroxypropyl methylcellulose; and
   iv) wherein the composition is in a time release formulation that is a tablet, pill, or capsule.

2. The vitamin composition of claim 1, wherein:
   i) the Zinc is about 8.50 mg;
   ii) the Selenium is about 50.0 micrograms (mcg);
   iii) the Vitamin B1 is about 0.23 mg;
   iv) the Vitamin B2 is about 0.10 mg;
   v) the Niacin is about 7.00 mg;
   vi) the Vitamin B6 is about 0.25 mg;
   vii) the Folate is about 85.0 mcg;
   ix) the Vitamin B12 is about 2.20 mcg;
   x) the Vitamin B5 is about 1.70 mg;
   xi) the Vitamin E is about 3.50 mg;
   xii) the Vitamin K2 is about 45.00 mcg;
   xiii) the GSH is about 670.0 mg;
   xiv) the SOD is about 33.0 mg; and
   xv) the CAT is about 245.0 mg.

3. The vitamin composition of claim 1, wherein the inactive ingredient is hydroxypropyl methylcellulose that acts as a pharmaceutical adjunct to provide a sustained release of the active ingredients.

4. A vitamin composition for use in a safe and low risk malnutrition treatment while slowing kidney disease progression in Chronic Kidney Disease Patients, comprising:
   i) active ingredients consisting of: Zinc; Selenium; Vitamin B1; Vitamin B2; Niacin; Vitamin B6; Folate; Vitamin B12; Vitamin B5; Vitamin E; Vitamin K2; and
   ii) excluding all of the following: calcium (Ca); magnesium (Mg); phosphorus (P); sodium (Na); manganese (Mn); fluoride (F); Vitamin D; and Vitamin K1;
   iii) a non-naturally occurring inactive ingredient comprising one or more of: microcrystalline cellulose, and hydroxypropyl methylcellulose; and
   iv) wherein the composition is in a time release formulation that is a tablet, pill, or capsule.

5. The vitamin composition of claim 4, wherein:
   i) the Zinc is about 9.0 mg;
   ii) the Selenium is about 50.0 micrograms (mcg);
   iii) the Vitamin B1 is about 0.23 mg;
   iv) the Vitamin B2 is about 0.10 mg;
   v) the Niacin is about 7.00 mg;
   vi) the Vitamin B6 is about 0.25 mg;
   vii) the Folate is about 85.0 mcg;
   ix) the Vitamin B12 is about 2.20 mcg;
   x) the Vitamin B5 is about 1.70 mg;
   xi) the Vitamin E is about 3.50 mg;
   xii) the Vitamin K2 is about 45.00 mcg.

* * * * *